US006716234B2

(12) United States Patent
Grafton et al.

(10) Patent No.: US 6,716,234 B2
(45) Date of Patent: Apr. 6, 2004

(54) HIGH STRENGTH SUTURE MATERIAL

(75) Inventors: R. Donald Grafton, Naples, FL (US); D. Lawson Lyon, Exeter (GB); Brian Hallet, Taunton (GB)

(73) Assignee: Arthrex, Inc., Naples, FL (US)

( * ) Notice: Subject to any disclaimer, the term of this patent is extended or adjusted under 35 U.S.C. 154(b) by 5 days.

(21) Appl. No.: 09/950,598

(22) Filed: Sep. 13, 2001

(65) Prior Publication Data

US 2003/0050666 A1 Mar. 13, 2003

(51) Int. Cl.[7] ................................................. A61L 17/04
(52) U.S. Cl. ....................................................... 606/228
(58) Field of Search ......................................... 606/228

(56) References Cited

U.S. PATENT DOCUMENTS

| | | | |
|---|---|---|---|
| 3,942,532 A | | 3/1976 | Hunter et al. |
| 4,047,533 A | * | 9/1977 | Perciaccante et al. ........ 606/230 |
| 4,344,908 A | | 8/1982 | Smith et al. ................. 264/203 |
| 4,411,854 A | | 10/1983 | Maurer et al. ............... 264/205 |
| 4,422,993 A | | 12/1983 | Smith et al. ............... 264/210.8 |
| 4,430,383 A | | 2/1984 | Smith et al. ................. 428/364 |
| 4,436,689 A | | 3/1984 | Smith et al. ................. 264/204 |
| 4,668,717 A | | 5/1987 | Lemstra et al. .............. 523/322 |
| 5,019,093 A | * | 5/1991 | Kaplan et al. ............... 606/228 |
| 5,067,538 A | | 11/1991 | Nelson et al. ................ 152/451 |
| 5,234,764 A | | 8/1993 | Nelson et al. ............... 428/364 |
| 5,261,886 A | * | 11/1993 | Chesterfield et al. ........ 606/228 |
| 5,318,575 A | | 6/1994 | Chesterfield et al. ........ 606/151 |
| 5,383,925 A | * | 1/1995 | Schmitt ...................... 623/1.53 |
| 5,403,659 A | | 4/1995 | Nelson et al. ............... 428/364 |
| 5,540,703 A | | 7/1996 | Barker, Jr. et al. |
| 5,630,976 A | | 5/1997 | Nelson et al. ............ 264/210.8 |
| 5,720,765 A | * | 2/1998 | Thal ........................... 606/232 |
| 6,045,571 A | * | 4/2000 | Hill et al. .................... 606/228 |
| 6,063,105 A | * | 5/2000 | Totakura ..................... 606/228 |

FOREIGN PATENT DOCUMENTS

EP 0561108 A2 9/1993

OTHER PUBLICATIONS

"SecureStrand™ Cable System," Surgical Dynamics, Inc. 1999.

* cited by examiner

Primary Examiner—David O. Reip
(74) Attorney, Agent, or Firm—Dickstein Shapiro Morin & Oshinsky, LLP

(57) ABSTRACT

A high strength abrasion resistant surgical suture material with improved tie down characteristics. The suture features a multifilament cover formed of braided strands of ultra high molecular weight long chain polyethylene and polyester. The cover surrounds a core formed of twisted strands of ultrahigh molecular weight polyethylene. The suture, provided in a #2 size, has the strength of #5 Ethibond, is ideally suited for most orthopedic procedures, and can be attached to a suture anchor or a curved needle.

9 Claims, 2 Drawing Sheets

HIGH STRENGTH SUTURE MATERIAL

BACKGROUND OF THE INVENTION

1. Field of the Invention

The present invention relates to high strength surgical suture materials, and more particularly to braided suture blends of ultrahigh molecular weight polyethylene and polyester having high strength and excellent tie down characteristics.

2. Description of the Related Art

Suture strength is an important consideration in any surgical suture material. One of the strongest materials currently formed into elongated strands is an ultrahigh molecular long chain weight polyethylene, typically used for fishing line and the like, which is sold under the trade names Dyneema or Spectra. However, this material, while much stronger than ordinary surgical suture, does not have acceptable knot tie down characteristics for use in surgical applications.

SUMMARY OF THE INVENTION

The present invention advantageously provides a high strength surgical suture material with improved tie down characteristics. The suture features a braided cover made of a blend of ultrahigh molecular weight long chain polyethylene and polyester. The polyethylene provides strength. The polyester provides improved tie down properties.

The preferred suture includes a multifilament cover formed of a plurality of fibers of ultrahigh molecular weight polyethylene braided with fibers of polyester. The cover surrounds a core of twisted fibers of ultrahigh molecular weight polyethylene.

Preferably, the ultrahigh molecular weight polyethylene includes about 60% of the cover fibers, with polyester making up about 40% of the cover filaments. The core comprises about 30% of the suture, the cover making up about 70%. As an enhancement, the suture is provided with a coating on the cover, as is known in the prior art. The suture can be packaged ready for use attached to a suture anchor.

Ultrahigh molecular weight polyethylene fibers suitable for use in the present invention are marketed under the Dyneema trademark by Toyo Boseki Kabushiki Kaisha.

The suture of the present invention advantageously has the strength of Ethibond #5 suture, yet has the diameter, feel and tie ability of #2 suture. As a result, the suture of the present invention is ideal for most orthopedic procedures such as rotator cuff repair, archilles tendon repair, patellar tendon repair, ACL/PCL reconstruction, hip and shoulder reconstruction procedures, and replacement for suture in anchors.

Other features and advantages of the present invention will become apparent from the following description of the invention which refers to the accompanying drawings.

BRIEF DESCRIPTION OF THE DRAWING(S)

DETAILED DESCRIPTION OF THE PREFERRED EMBODIMENTS

Figure 1:
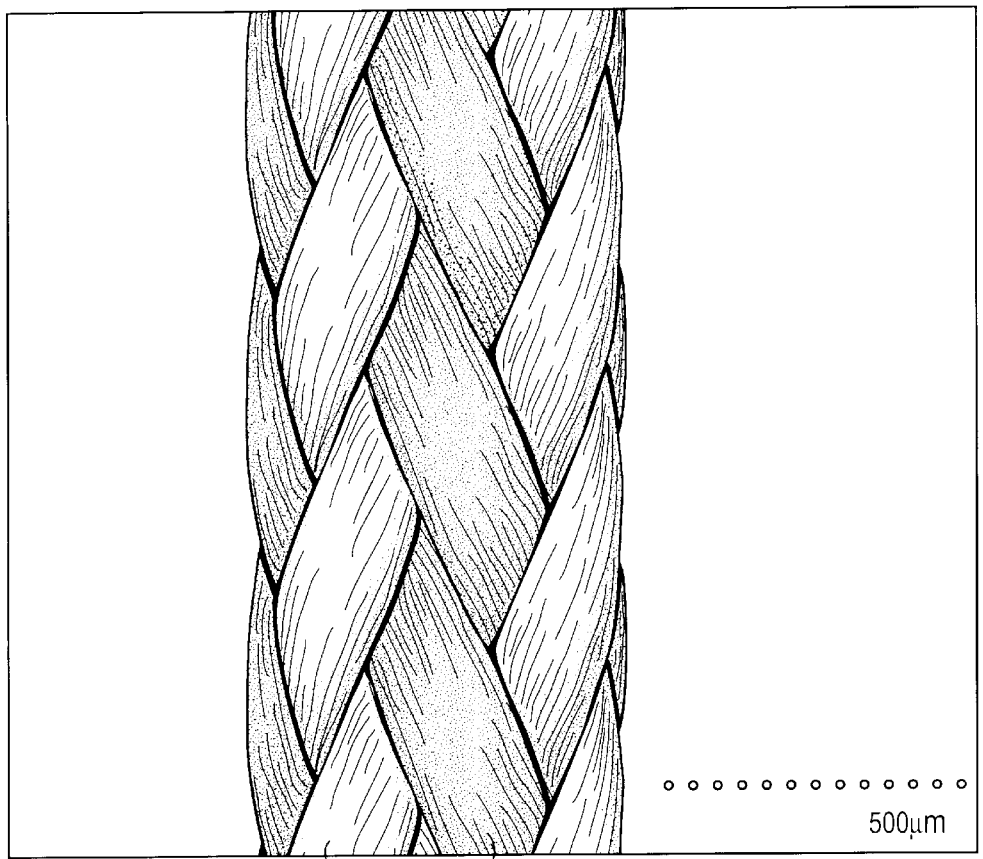
FIG. 1 is a copy of a scanning electron micrograph of a length of suture according to the present invention.
Figure 2:
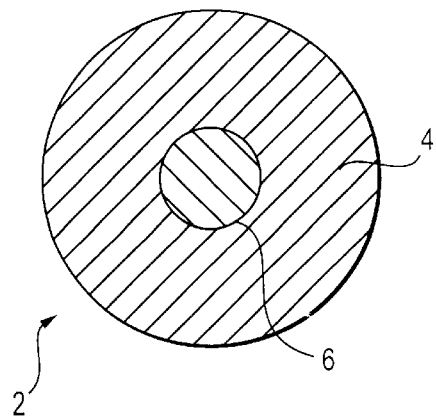
FIG. 2 is a schematic cross section of a length of suture according to the present invention.

Referring to FIG. 1, a scanning electron micrograph of a length of suture 2 according to the present invention is shown. Suture 2 is made up of a cover 4 and a core 6 surrounded by the cover. See FIG. 2. Strands of ultrahigh molecular weight polyethylene (UHMWPE) 8, sold under the tradename Dyneema or Spectra, and strands of polyester 10 are braided together to form the cover 4. The core is formed of twisted UHMWPE.

Details of the present invention will be described further below in connection with the following examples:

EXAMPLE 1

USP Size 5 (EP size 7)

Made on a 16 carrier Hobourns machine, the yarns used in the braided cover are polyester type 712 and Dyneema SK65. The cover is formed using eight carriers with one end of 190 d'tex polyester per carrier, and eight carriers with one end of 220 d'tex Dyneema per carrier. The core is formed of Dyneema using one end of 440/1/3 twisted 10 tpi "z" and 7 tpi "s" (core is not steam set). Picks per inch (PPI)=36. In forming the suture, the percent cover is 71.31, while the percent of the core is 28.69. Runnage is 1991 meters per kilo.

Of the overall suture, the polyester in the cover (8 carriers×190 d'tex=1520 d'tex) makes up 33.04% of the suture, and the Dyneema in the cover (8 carriers×220 d'tex=1760 dtex) makes up 38.76% of the suture. The Dyneema core (3 carriers×440 d'tex=1320 d'tex) is 28.69% of the suture.

EXAMPLE 2

USP Size 2

The suture is 38.09% polyester, 61.91% UHMWPE, or about 40% polyester and about 60% UHMWPE.

The examples above are for size 2 and size 5 sutures. In the making of various sizes of the inventive suture, different decitex values and different PPI settings can be used to achieve the required size and strength needed. In addition, smaller sizes may require manufacture on 12 carrier machines, for example. The very smallest sizes are made without a core. Overall, the suture may range from 5% to 90% ultrahigh molecular weight polymer (Dyneema), with the balance formed of polyester.

The suture is preferably coated with a silicon based coating to fill in voids and provide optimum run down.

The Dyneema component of the present invention provides strength, and the polyester component is provided to improve tie ability and tie down characteristics. However, it has been found that the Dyneema provides an unexpected advantage of acting as a cushion for the polyester fibers, which are relatively hard and tend to damage each other. The Dyneema prevents breakage by reducing damage to the polyester when the suture is subjected to stress.

According to an alternative embodiment of the present invention, a partially bioabsorbable suture is provided by blending a high strength material, such as UHMWPE fibers, with a bioabsorbable material, such as PLLA or one of the other polylactides, for example. Accordingly, a suture made with about 10% Dyneema blended with absorbable fibers would provide greater strength than existing bioabsorbable suture with less stretch. Over time, 90% or more of the suture would absorb, leaving only a very small remnant of the knot.

Figure 3:
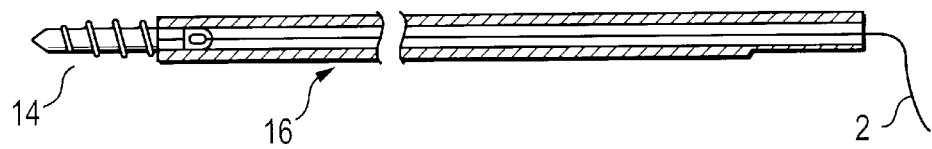
FIG. 3 is an illustration of the suture of the present invention attached to a suture anchor.
Figure 4A:
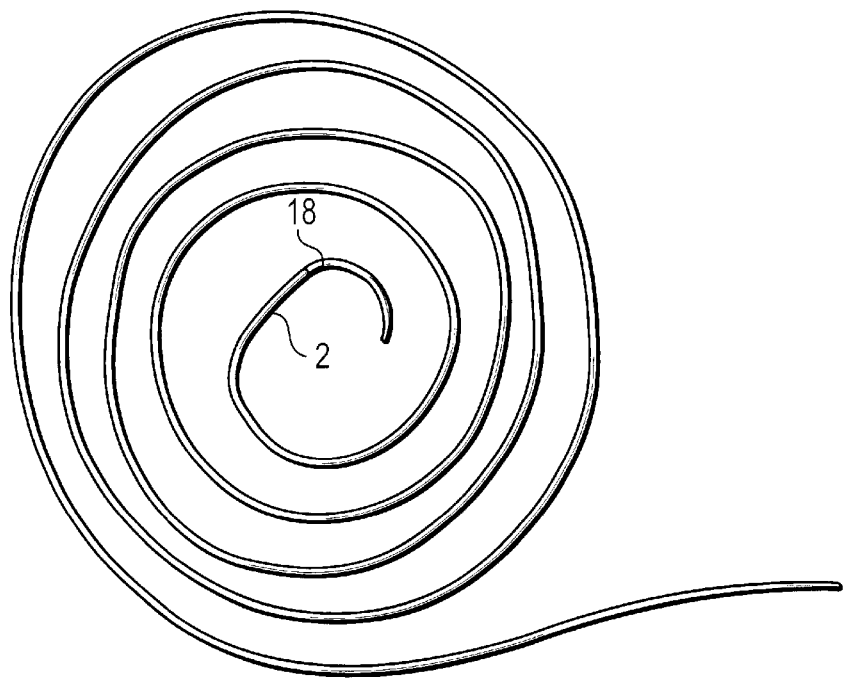
FIGS. 4A and 4B show the suture of the present invention attached to a half round, tapered needle.
Figure 4B:
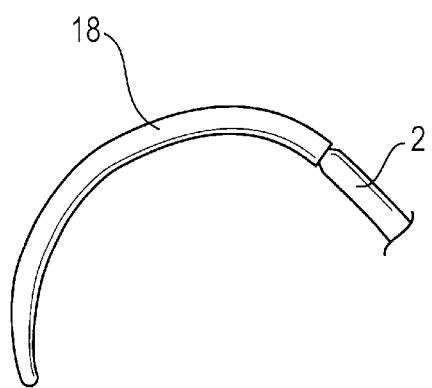

In one method of using the suture of the present invention, the suture 2 is attached to a suture anchor 14 as shown in FIG. 3 (prepackaged sterile with an inserter 16), or is attached to a half round, tapered needle 18 as shown in FIGS. 4A and 4B.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A suture filament suitable for use as a suture or ligature comprising:

a cover formed of a plurality of braided fibers of ultrahigh molecular weight polyethylene and polyester; and a core of twisted ultrahigh molecular weight polyethylene surrounded by the cover.

2. The suture filament of claim 1, wherein the ultrahigh molecular weight polyethylene comprises about 60% of the braided fibers.

3. The suture filament of claim 1, wherein the polyester comprises about 40% of the braided fibers.

4. The suture filament of claim 1, wherein the core comprises a bout 30% of the filament.

5. The suture filament of claim 1, wherein the cover comprises about 70% of the filament.

6. The suture filament of claim 1, further comprising a coating disposed on the cover.

7. The suture filament of claim 1, wherein the polyester is non-absorbable.

8. A suture assembly comprising:

a suture having a multifilament cover formed of a plurality of braided fibers of ultrahigh molecular weight polyethylene and fibers of polyester;

a core formed of twisted fibers of ultrahigh molecular weight polyethylene; and a suture anchor attached to the suture.

9. A suture assembly comprising:

a suture having a multifilament cover formed of a plurality of braided fibers of ultrahigh molecular weight polyethylene and fibers of polyester;

a core formed of twisted fibers of ultrahigh molecular weight polyethylene; and a half round, tapered needle attached to the suture.

* * * * *